United States Patent
Gretz et al.

(10) Patent No.: US 9,861,315 B2
(45) Date of Patent: Jan. 9, 2018

(54) ADHESIVE FUNCTIONAL STRIP FOR TRANSCUTANEOUS FLUORESCENCE MEASUREMENT

(71) Applicants: Lohmann GmbH & Co. KG, Neuwied (DE); Norbert Gretz, Mannheim (DE); Daniel Schock-Kusch, Mannheim (DE)

(72) Inventors: Norbert Gretz, Mannheim (DE); Daniel Schock-Kusch, Mannheim (DE); Michael Herbertz, Wermelskirchen (DE); Ralf Nittenwilm, Hoehr-Grenzhausen (DE)

(73) Assignee: Lohmann GMBH & Co. KG, Neuwied (DE)

( * ) Notice: Subject to any disclaimer, the term of this patent is extended or adjusted under 35 U.S.C. 154(b) by 257 days.

(21) Appl. No.: 14/427,889

(22) PCT Filed: Sep. 4, 2013

(86) PCT No.: PCT/DE2013/000499
§ 371 (c)(1),
(2) Date: Mar. 12, 2015

(87) PCT Pub. No.: WO2014/040580
PCT Pub. Date: Mar. 20, 2014

(65) Prior Publication Data
US 2015/0245799 A1  Sep. 3, 2015

(30) Foreign Application Priority Data

Sep. 13, 2012 (DE) .......................... 10 2012 018 076

(51) Int. Cl.
*A61B 5/1455* (2006.01)
*A61B 5/00* (2006.01)
(Continued)

(52) U.S. Cl.
CPC .......... *A61B 5/6832* (2013.01); *A61B 5/0071* (2013.01); *A61B 5/02* (2013.01);
(Continued)

(58) Field of Classification Search
CPC ... A61B 5/0002; A61B 5/0059; A61B 5/1455; A61B 5/14551; A61B 5/14552; A61B 5/14532; A61B 5/683; A61B 5/6832
See application file for complete search history.

(56) References Cited

U.S. PATENT DOCUMENTS

| 4,830,014 A | * | 5/1989 | Goodman | .......... A61B 5/14552 600/310 |
| 5,054,488 A | * | 10/1991 | Muz | .................. A61B 5/14552 600/344 |

(Continued)

FOREIGN PATENT DOCUMENTS

| DE | 32 24 641 A1 | 1/1984 |
| DE | 10 2008 050 347 A1 | 4/2010 |

(Continued)

OTHER PUBLICATIONS

Search Report issued in corresponding International Application No. PCT/DE2013/000499, dated Dec. 20, 2013 (3 pages).

(Continued)

*Primary Examiner* — Eric Winakur
*Assistant Examiner* — Chu Chuan (JJ) Liu
(74) *Attorney, Agent, or Firm* — Bookoff McAndrews, PLLC

(57) ABSTRACT

The present invention pertains to a functional patch to be affixed to the skin, with the aim of measuring metabolic disruptions to organs, and general organ functions, of kidneys, liver, heart, pancreas and muscles (lactate), for example—more particularly it concerns the measurement of the glomerular filtration rate (GFR)—and also to a method for producing a functional patch of this kind.

11 Claims, 6 Drawing Sheets

(51) Int. Cl.
  *A61B 5/20* (2006.01)
  *C09J 7/02* (2006.01)
  *A61B 5/02* (2006.01)
  *A61B 5/145* (2006.01)
  *C08K 3/04* (2006.01)
  *C09J 133/08* (2006.01)

(52) U.S. Cl.
  CPC ........ *A61B 5/1455* (2013.01); *A61B 5/14532* (2013.01); *A61B 5/14546* (2013.01); *A61B 5/201* (2013.01); *A61B 5/425* (2013.01); *A61B 5/4244* (2013.01); *A61B 5/6833* (2013.01); *C09J 7/0246* (2013.01); *A61B 2560/0285* (2013.01); *A61B 2562/12* (2013.01); *C08K 3/04* (2013.01); *C09J 133/08* (2013.01); *C09J 2201/134* (2013.01); *C09J 2201/606* (2013.01); *C09J 2205/102* (2013.01); *C09J 2400/22* (2013.01); *C09J 2421/00* (2013.01); *C09J 2433/00* (2013.01); *C09J 2467/006* (2013.01); *C09J 2483/00* (2013.01); *C09J 2483/005* (2013.01)

(56) References Cited

U.S. PATENT DOCUMENTS

| | | | | |
|---|---|---|---|---|
| 5,402,777 A * | 4/1995 | Warring | ............ | A61B 5/14552 600/334 |
| 5,830,136 A | 11/1998 | Delonzor et al. | | |
| 5,989,298 A | 11/1999 | Lehmann | | |
| 6,415,167 B1 * | 7/2002 | Blank | ................. | A61B 5/1455 600/310 |
| 6,530,915 B1 * | 3/2003 | Eppstein | ............ | A61B 5/14532 600/309 |
| 6,745,061 B1 * | 6/2004 | Hicks | ................. | A61B 5/14552 600/323 |
| 6,748,254 B2 * | 6/2004 | O'Neil | ................. | A61B 5/6814 600/323 |
| 7,813,536 B2 | 10/2010 | Ma et al. | | |
| 2003/0019115 A1 | 1/2003 | Tannenbaum | | |
| 2006/0229508 A1 | 10/2006 | Kermani et al. | | |
| 2007/0032721 A1 | 2/2007 | Crane et al. | | |

FOREIGN PATENT DOCUMENTS

| | | |
|---|---|---|
| DE | 10 2010 047 215 A1 | 3/2012 |
| DE | 10 2011 012 674 B3 | 4/2012 |
| EP | 0 421 697 A2 | 4/1991 |
| EP | 1 111 387 A1 | 6/2001 |
| EP | 1 213 037 A1 | 6/2002 |
| EP | 1 632 320 A1 | 3/2006 |
| EP | 1 752 085 A2 | 2/2007 |
| WO | WO 2010/020673 A2 | 2/2010 |

OTHER PUBLICATIONS

Notice of Reasons for Rejection dated Aug. 1, 2007 in Japanese Application No. 2015-531463 and English Translation (4 pages).

* cited by examiner
ADHESIVE FUNCTIONAL STRIP FOR TRANSCUTANEOUS FLUORESCENCE MEASUREMENT This application is the U.S. national phase entry under 35 U.S.C. §371 of International Application No. PCT/DE2013/000499, filed on Sep. 4, 2013, which claims priority to German Patent Application No. DE 10 2012 018 076.4, filed on Sep. 13, 2012, the entireties of each of which are incorporated by reference herein.

The present invention relates to a functional patch for measuring metabolic organ disorders and general organ functions of e.g. the kidneys, the liver, the heart, the pancreas and the muscles (lactate)—in particular, it relates to the measurement of the glomerular filtration rate (GFR)—and also to a method for producing a functional patch of this type. The glomerular filtration rate indicates the total volume of primary urine by the glomeruli (knots of capillary vessels) of both kidneys together, measured over a defined unit of time, i.e. the volume of the largely protein-free, unconcentrated urine which is formed by the renal corpuscles upon perfusion of the kidneys. These are approx. 0.12 liters per minute or approx. 170 liters per day for humans with normal blood-pressure readings. The GFR drops physiologically with increasing age, or pathologically in the case of very widely-varying types of renal disease. The GFR is the most important quantity for assessing renal function. In daily clinical practice, it is determined approximately by determining the creatinine clearance. That volume of plasma which is cleared of a particular substance per unit of time is referred to as "clearance". In order to be able to determine the GFR, the clearance of a marker substance, i.e. a substance which is eliminated from an organ with a specific half-life and which is neither secreted nor resorbed back in the tubule system of the kidney, is observed. A distinction is made here between exogenous markers, which are supplied to the body from the outside by injection or infusion, and endogenous markers produced naturally in the body. Of the first-named group, preferably inulin, a physiologically inert polysaccharide, is used as indicator substance. Alternatively, nowadays however also e.g. contrast media and radioactively marked substances are also used as exogenous marker substances. Since however on one hand inulin is difficult to measure and on the other hand the entire procedure involves fairly great expense, determination of the clearance by means of marker substances takes place as a rule only in the context of scientific investigations.

Markers which involve considerably less expense for clinical and ambulant routine diagnostics and are therefore also used in preference in daily clinical practice are endogenous markers such as creatinine, a metabolic product which has to be excreted via the urine and hence via the kidney, or cystatin C, a protein produced naturally in the body.

The novel functional patch according to the invention is used in the context of the principle of transcutaneous fluorescence measurement. In this, first of all the patient is injected with a fluorescent indicator substance which is specific for one organ. An indicator substance of this type is marked with a dye which can be detected optically by a transcutaneous fluorescence measurement. An inference about the proper functioning of the organ can be drawn using the concentration of the marker, taking into account the concentration-time curve produced in each case. The concentration of such a substance rapidly increases in the tissue after injection. If the substance is then excreted again, the concentration drops. The half-life of this drop is a measurement of the organ function: if the half-life is short, the function of the organ is good, and vice versa.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows.

Figure 1:
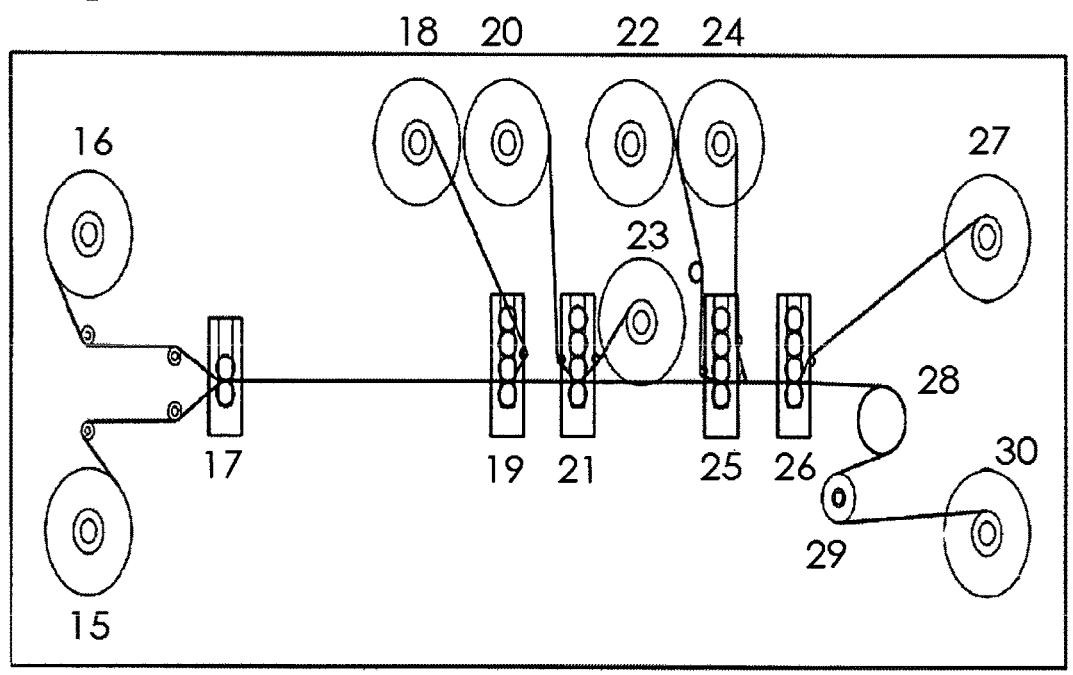
FIG. 1 is a schematic, side view illustration of an exemplary system for producing a sealing frame, according to aspects of the present disclosure.
Figure 2:
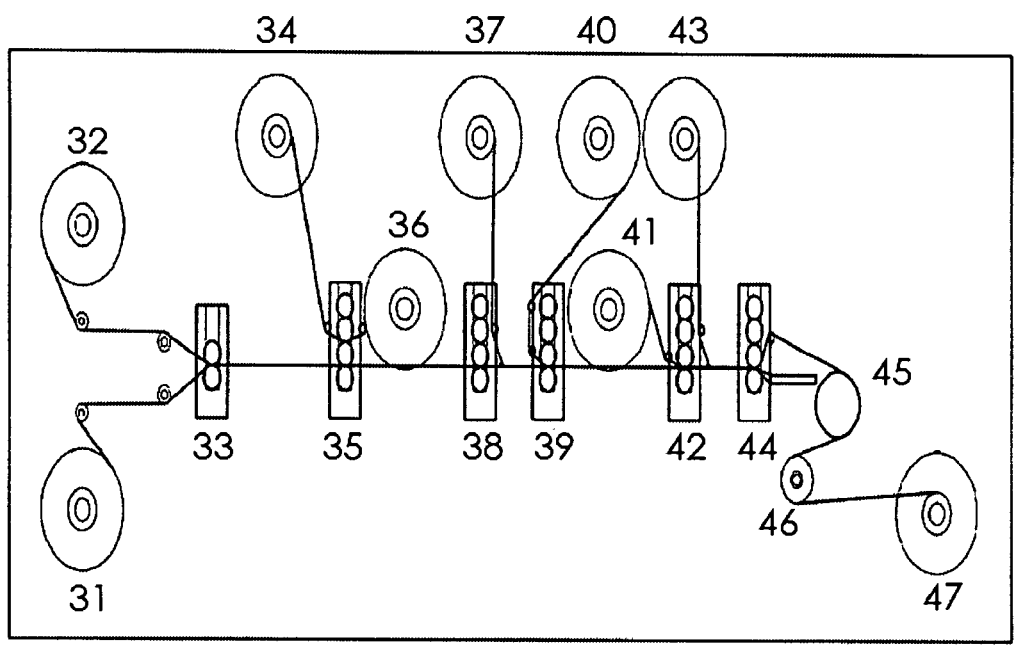
FIG. 2 is a schematic, side-view illustration of an exemplary system for performing a punching process, according to aspects of the present disclosure.

The principle of fluorescence measurement, which is known per se, is to detect the light radiation produced by fluorescence: in principle, in this case the excitation light irradiates the sample which contains the fluorescent substance. This fluorescent substance converts part of the incident light of a certain wavelength into fluorescent light of a higher wavelength. The light thus produced beams in all directions and can be measured with a detector e.g. perpendicular to the axis of the incident light.

It is essential in this case, in order to obtain objective and meaningful measured values, to rule out as far as possible factors which might distort the measurement, such as in particular the incidence of diffused light. This diffused light may e.g. be caused by cloudiness as a result of the presence of solids, or alternatively also if the sensor is applied to the skin in a non-light-tight manner, owing to the lateral incidence of light which then ensues.

Otherwise, the essential difference with such tests lies in the use of different markers which fluoresce at different wavelengths and penetrate to different depths dependent on wavelength.

In addition to the use of different marker substances, which will not be discussed in greater detail at this point, over the course of time more and more new measuring methods have been and are being tested and also claimed in the patent literature. In older protective rights such as DE 32 24 641 A1, GFR determination by means of HPLC is claimed; in more recent ones, determination by means of magnetic resonance therapy (DE 10 2008 050 347 B4), CT (U.S. Pat. No. 7,813,536 B2) or measurement of the UV absorbance of at least one substance which has to be excreted via the urine in the dialysate outflow or in the blood flow of the blood treatment unit (DE 10 2010 047 215 A1 and DE 10 2011 012 674 B3). EP 0 421 697 A2 describes—as also happens in a similar form in some further protective rights—an imaging magnetic resonance method for determining the GFR; EP 1 111 387 B1 deals with immunological analysis methods. EP 1 632 320 B1 in this connection has as its theme generally immunoanalytical techniques, chromatographic techniques, mass spectrometry, imaging techniques and radioactive counting techniques, and the core of U.S. Pat. No. 5,989,298 A is a capillary electrophoresis method.

US 2003/0019115 A1, finally, claims a user-friendly, portable, electronic device which in a very short time calculates data of a measurement method, not specified further, for patient-specific GFR.

In the course of a desired further simplification of the investigation of organ functions, there are now methods, by means of newly-developed equipment, for determining the respective organ functions and here in particular the GFR, but also the functions of the liver, the heart, the pancreas, or metabolic functions, transcutaneously and not by blood tests.

In these methods, electronic sensors are fastened to the skin of the test person over a defined period. By means of a self-adhesive coupling layer, the sensor is held on the skin in a defined position over a defined period in as pressure-free a manner as possible and without disrupting the microcirculation of the skin (cf. Lim et al.: "Probe pressure effects on human skin diffuse reflectance and fluorescence spectroscopy measurements" in: Journal of Biomedical Optics 16(1), January 2011), and once the investigation has been terminated it is also removed from the skin again without leaving any residue and also without irritation or injury to skin cell tissue. The closest prior art here is WO 2010/020673 A2, in which a sensor patch for transcutaneous measurement of an organ function, in particular the renal function, is proposed, wherein the body surface is irradiated with at least one scanning or excitation light and a detector detects the response light radiated in from the direction of the body surface. The patch described in this WO is preferably constructed such that the beam source is an integral component of the patch: statements relating to demands made on the patch and also its structure are given merely in a very generalised form in the aforementioned WO application. In this case, it is precisely this point which plays a significant role, because as already mentioned an essential demand made the patch is that its geometry and overall construction be designed such that diffused light is absorbed and the fluorescence measurement is not disrupted. This requires the sensor head to have to be attached to the skin in a light-tight manner in order to prevent diffused light from penetrating, but on the other hand it must also not sit too tightly thereon, since otherwise the microcirculation in the skin is disrupted. This in turn would lengthen the half-lives and distort the measured values.

This requirement has been met by an adhesive patch of multilayer structure in which, unlike in WO 2010/020673 A2, the beam source is not an integral component of the patch inside a laminar structure, the term "patch" here covering all possible types of an object in film form provided with an adhesive coating: the entire sensor element is decoupled from the patch proper, and is applied to the patch as a separate part. Thus, therefore, both the patch and the sensor can be used several times, or alternatively also be used as an article which can be used only once and then has to be disposed of. The specific multilayer structure of the patch on one hand prevents the diffused light, which may in part also "travel" laterally in the skin, from reaching the photodiode, since light beamed in the vicinity is absorbed, and on the other hand prevents parts of the skin from penetrating into the sensor head from below once the sensor head has been placed on. In the latter case, the perfusion in the penetrated tissue which at the same time is however also used for the measurement would be slowed down. This would also slow down the excretion of the marker from the tissue thus pinched, and the measured curve shape would likewise be slower, and the measurement result would therefore be distorted. Such disruption of the microcirculation is prevented by the lowermost, continuous and transparent layer of the patch. The adhesive patch according to the invention represents a method for measuring organ functions, and here in particular renal function, which is simple to implement, but at the same time is inexpensive, quick and reliable.

Figure 3:
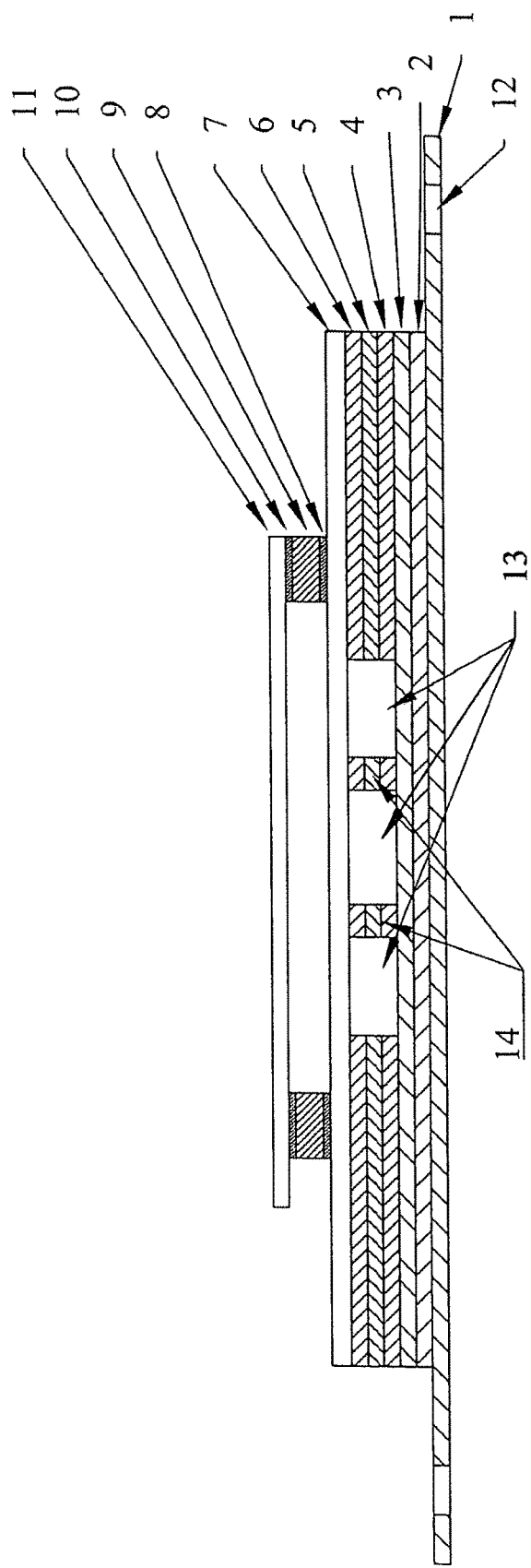
FIG. 3 illustrates a cross-sectional view of an exemplary functional patch, according to aspects of the present disclosure.
Figure 4:
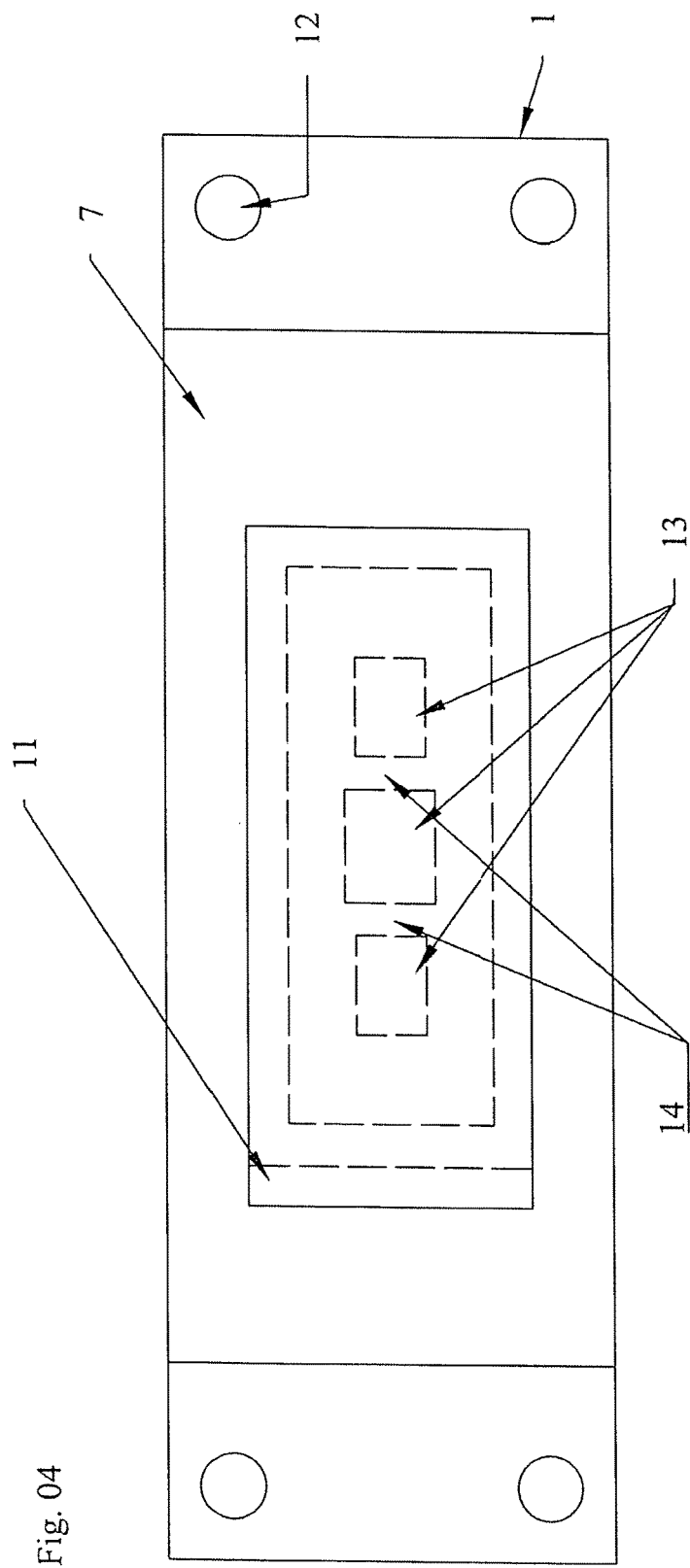
FIG. 4 illustrates a top view of an exemplary functional patch, according to aspects of the present disclosure.

The sandwich-like construction of the patch, which is preferably in the form of a shaped punched part, from a plurality of layers will be explained in greater detail below with reference to FIG. 3. This shaped punched part initially has on the side facing the skin a film which covers the adhesive surface towards the skin as a release liner (1). For this liner, as for all liners used in the sandwich-like structure, a gradated siliconised polyester film is preferred. The gradation, i.e. the ratio of the release values of the two liner sides, in this case should be between 1:2 and 1:10. The gradation in this case, dependent on the adhesive strength of the adhesive, is adapted to the requirements of secure fixing of the punched part even when winding onto rolls. The film, however, has a further function: it has an excess length with positioning holes (12) on both sides which goes beyond the adhesive surface in each case. These positioning holes, during the production of the entire functional part comprising the sensor and the patch, serve for fastening the sensor to the patch with a precise fit. The liner covers a biocompatible adhesive layer (2), which is approved for medical use on the skin, on the basis of either acrylate, silicone or rubber until it is used. A transparent polyester film (3) is applied to that side of this adhesive layer which is remote from the skin. Instead of two separate components such as a backing-less transfer pressure-sensitive adhesive tape (2) and the polyester film (3), here however a pressure-sensitive adhesive tape which is adhesive on one side, with a transparent backing material and a biocompatible adhesive layer, would also be able to be used, as a result of which a lamination operation could be dispensed with during production and hence also costs would be lowered.

The transparent polyester film is glued with an adhesive (4) which is modified to be dark-coloured, preferably black. For reasons of stability, in the context of the punching operation during the production of the patch, here a tape (4-6) which is provided on both sides with a pressure-sensitive adhesive coating with a dark/black adhesive (4, 6) will be most suitable, but it would also be entirely possible to use a backing-less transfer tape. This/these dark adhesive layer(s) contain(s) at least one recess, above which the sensor head is positioned when the complete functional part comprising the patch and the sensor is assembled. This recess, produced e.g. by means of a punching operation, represents an optical window which enables the sensor to examine the skin undisturbed with its LEDs and photodiodes.

The adhesive layer (6) remote from the first polyester film (3) is covered by a further transparent polyester film (7) which covers the at least one recess and hence also stabilises the entire system, on which film finally a circumferential frame (8-10), e.g. made from a foam backing material (11) which is provided on both sides with a pressure-sensitive adhesive coating and is punched corresponding to requirements and before use is covered by a liner with a protruding grip tab, is applied by gluing. This frame (8-10) serves to prevent the incidence of diffused light which might distort the measurement results. In the particularly preferred case, this frame is an integral component of the functional patch, but a sealing frame separate from the functional patch would also be conceivable, which frame would then be present as a separate component which is adhesive on both sides, or alternatively only on one side, and would be applied to the functional patch at the appropriate point before applying the sensor. In a further form of application, the sealing frame could also be fastened permanently to the sensor, in which case it would then in principle be glued on to the functional patch together with the sensor.

EXAMPLE OF THE STRUCTURE OF THE FUNCTIONAL PATCHES

In the successful tests with this structure, the transfer adhesive "DuploMED VP 8171", which is suitable for medical applications, was used as a coupling layer towards the skin, a tape which, like the adhesive tapes mentioned here below, is an adhesive tape produced and sold by the company "Lohmann GmbH & Co. KG", in this case a transfer adhesive tape (2) 50 μm thick with a silicone paper covering. The pressure-sensitive adhesive is a biocompatible solvent-based polyacrylate adhesive which consists of two components: the polyacrylate solution and a crosslinker solution. It meets the requirements of DIN EN 10993-1, and is predominantly used in medical patches, films and other adhesive dressing materials. The pressure-sensitive adhesive is coated on a coating installation approved for medical manufacture in a roller application process in a thickness of 50 μm onto a siliconised 90 g/m$^2$ kraft paper, is dried and cross-linked. The original silicone paper covering is replaced for the functional patch manufacturing operation by a 50 μm thick, siliconised polyethylene terephthalate release film (1).

The transparent adhesive layer (2) in the applications provided here also acts as a diffuser, and thus permits the use of very small punctiform LEDs in the sensor. The use of such LEDs is necessary in the context of the miniaturisation of the sensor head. In principle, however, any other adhesive which satisfies these conditions which are described can also be used here.

The transparent polyester film (3) glued with this transfer adhesive on the side remote from the skin serves to dimensionally stabilise the functional punched part frame and serves as a barrier or spacer between the medical (skin) and technical (sensor) side of the coupling layer. Towards the sensor, with "DuploCOLL® VP 6899" a 0.12 mm thick, double-sided pressure-sensitive adhesive tape with a 12 μm polyester backing (5) and a soot-pigmented, resin-modified solvent-based acrylate adhesive (4, 6) is used. The soot pigmentation imparts a light-absorbing function to the adhesive. In principle, however, here too again any adhesive systems which satisfy the conditions of very good gluing to the transparent polyester film (3) on the one hand and to the sensor housing on the other hand, and at the same time have a light-absorbing finish are suitable.

In the manufacturing process, at least one "window" (13) is punched out of the two black-pigmented adhesive layers (4-6) and also the corresponding polyester backing material (5), or recessed from the adhesive layer by suitable measures; in a preferred embodiment, a plurality of "windows" (13) located next to one another are punched or recessed, namely in such a way that the windows are separated from each other by narrow webs (14), so that also only one light source per window beams in. Above these windows, before use, the sensor head with LEDs and photodiode is attached in such a way that direct penetration of light from the LEDs into the photodiode is prevented by the black webs between the LEDs and the photodiode. That side of the black adhesive tape which is remote from the skin is covered by a transparent polyester film (7). This film (7), in addition to covering, also has the function of stabilising the edges of the patch which have been produced on the punched-out section or punched-out sections (13).

In order to prevent any laterally incident, and hence interfering, diffused light, that side of the black adhesive tape which is remote from the skin and is covered by the transparent film is finally also provided with a frame seal (8-10) which runs around the window or the windows. This seal preferably consists of a double-sided pressure-sensitive adhesive tape with a foam backing (9): in the present example this is "DuploCOLL® 9042", a pure acrylate pressure-sensitive adhesive (8, 10), coated on both sides of a polyethylene-vinyl acetate copolymer foam (9). As a result of the foam backing, this seal comprises a certain elasticity and flexibility which make it possible to react to and adapt to any movements of the sensor part.

Using relatively small numbers of this design which were produced in a "laser prototyping" process, reproducible measurement results were then achieved in a transcutaneous process—with this production process, in a discontinuous "sheet-to-sheet" process, individual sheets were machined manually with the aid of a flatbed laser such that finally prototypes of the functional patch were produced in small numbers.

Figure 5:
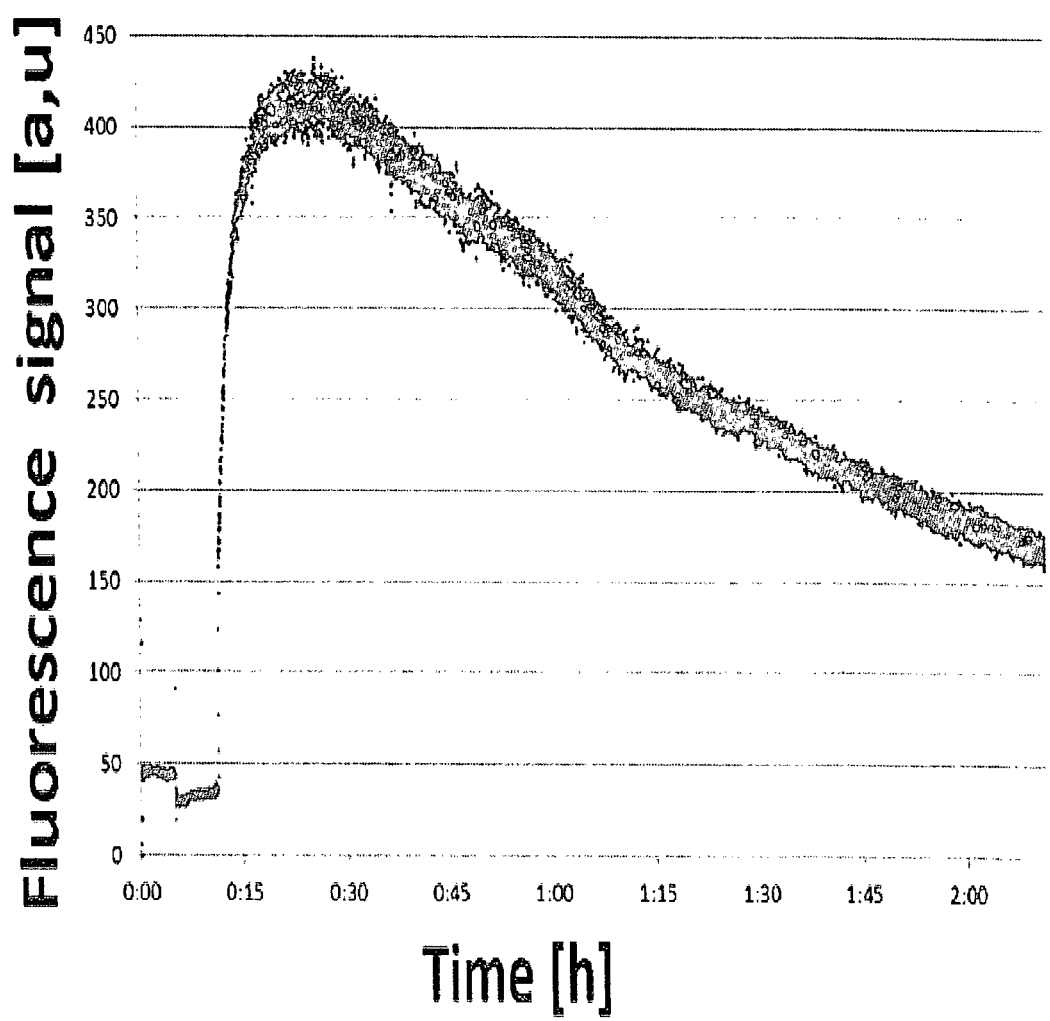
FIG. 5 illustrates an exemplary excretion curve, according to aspects of the present disclosure.
Figure 6:
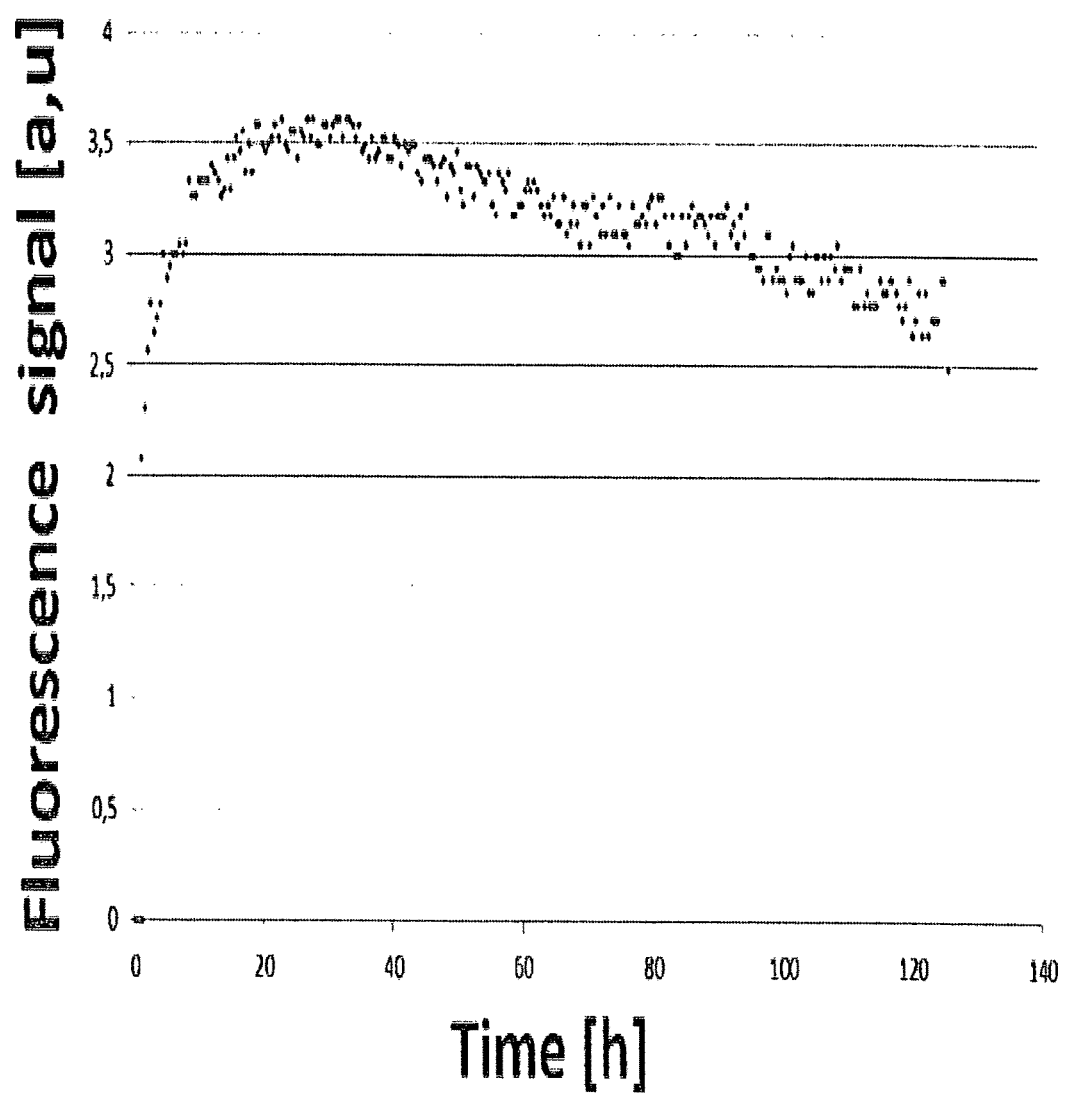
FIG. 6 illustrates another exemplary excretion curve, according to aspects of the present disclosure.

On the basis of initial tests with these prototypes, it was then demonstrated (cf. FIGS. 5 and 6) that the diffused light was absorbed and the microcirculation of the skin was not disrupted. FIG. 5 shows the excretion curve when using the functional patch according to the invention, and FIG. 6 shows the curve shape for a different type of fastening of the sensor to the skin: the curve in FIG. 6 has an atypically flattened form, a clear indication that the sensor was obviously fastened with increased pressure in order to prevent the incidence of diffused light, which in turn results in deformation of the skin layers and hence in an improper and distorted measurement result. The functional patch according to the invention was able to be detached again without leaving a residue and without leaving behind any injuries once the measurement had been ended.

Method of Production of the Functional Patch:

Machine production of the functional patch parts finally takes place preferably in a plurality of continuous "roll-to-roll" or "roll-to-sheet" lamination and punching processes, i.e. the individual components of the functional patch are mounted on rolls and in the punching process are successively and continuously unrolled at the points provided for this within the process and either processed in turn into rolls or alternatively into sheets with the actual functional patches.

In a first step, the sealing frame of the functional patch is produced. For this, initially the double-sided adhesive tape "Duplocoll 9042", which is covered with an HDPE film, is applied with a foam backing (16) in a laminating station (17) to a process film (15) provided with a weakly pressure-sensitive adhesive coating, which then in the further process acts as a punching base. In the next step, the contours of the sealing frame are punched out (19), and the punched screen is separated and rolled up (18). In the following step, the internal punch coverings are pulled off (21) with a cam tool and with the aid of a pull-off adhesive (20). This pull-off adhesive is a commercially available adhesive tape which is fed onto the composite in clocked manner in such a way that it merely comes always only partially into contact with the composite at precisely-defined specific intervals and in this manner also removes therefrom only the parts previously detached from the composite. These internal punch coverings which have been removed from the further production process are then rolled up (23) as well. In the following step, this procedure is repeated in principle: again, pull-off adhesive (22) is laminated (25) onto the punched-out parts which have still remained in the manufacturing process, which adhesive pulls off and rolls up (24) the punch covering and the internal adhesive parts. At the next station, the grip tab is punched (26), and subsequently the liner grid is pulled off and rolled up (27). The finished sealing frame is finally rolled up (30) via a transport roller (28) and a tension roll to the transport roller (29).

Independently of the production of the sealing frame, in parallel thereto in a second punching process the double-sided pressure-sensitive adhesive tape "Duplocoll 8171" (31) which is suitable for application to human skin is laminated (33) together with a non-siliconised 50 µm polyethylene terephthalate film (32). At the same time, in a reverse process the internal contour of the "Duplocoll VP 6899" tape (36) which is provided on both sides with a pressure-sensitive adhesive coating with black pigmented adhesive layers and which is covered with a punch covering is punched out (35), i.e. the "window", or in the case of several the "windows", is/are punched out.

Then the punch covering with the internal parts is pulled off (34), while the punched-out parts of the "DuploCOLL VP 6899" which are required for the further manufacturing process are now laminated together (38) with "Duplocoll 8171" (31) and also the polyethylene terephthalate film (32); at the same time, the original liner of the "Duplocoll VP 6899" is pulled off (37).

At the next laminating station (39), the 12 µm thick PETP film (40) is fed in. Following this, the sealing frame (30) already punched out in the first manufacturing step described above is laminated on (42) from the unwinding unit (41), before the process film (15) provided with a weakly pressure-sensitive adhesive coating is pulled off (43) from the entire system. Thus, the layered structure necessary for the method of operation of the system is now present, from which structure the final form of the functional patch according to the invention is punched out at a further punching station (44). The finished parts are then separated, and the remaining punched screen is wound up (47) via a transport roller (45) and a tension roll to the transport roller (46).

Use of the Functional Patches According to the Invention:

The functional patches according to the invention can be used in two forms: firstly, the patch and sensor part may be present as an inseparable unit, and then are also disposed of jointly after use, or they may be present separately and independently of each other and have to be put together just before use. In the latter case, e.g. a functional patch may also remain on the skin for a relatively long time and be equipped with different sensors in succession.

LIST OF REFERENCE NUMERALS

1=siliconised PETP film, with excess length and positioning holes
2=adhesive layer
3=PETP film, not siliconised,
4=adhesive layer
5=polyester film, not siliconised,
6=adhesive layer
7=PETP film, not siliconised,
8=adhesive layer
9=foam layer
10=adhesive layer
11=siliconised polyester film with grip tab
12=positioning holes
13=punched-out section
14=webs
15=infeed of weakly adhering process film
16=infeed of "DuploCOLL® 9042"
17=laminating station
18=rolling-up of punched screen
19=contour punch
20=pull-off adhesive roll
21=lamination of pull-off adhesive onto internal punch coverings
22=pull-off adhesive roll
23=rolling-up of pull-off adhesive with internal punch coverings
24=rolling-up of pull-off adhesive with external punch coverings and internal adhesive parts
25=lamination of pull-off adhesive onto external punch coverings and internal adhesive parts
26=grip tab punch
27=rolling-up of liner grid
28=transport roller
29=tension roll to the transport roller
30="sealing frame" product winding unit
31=infeed of "DuploCOLL® 8171"
32=infeed of PETP film, not siliconised
33=laminating station
34=rolling-up of punch covering with internal parts
35=internal contour punch
36=infeed of "DuploCOLL® VP 6899" covered with punch covering
37=rolling-up of original liner "DuploCOLL® VP 6899"
38=laminating station
39=laminating station
40=infeed of PETP film, not siliconised
41=infeed of prefabricated "sealing frame" punched parts
42=laminating station
43=rolling-up of weakly pressure-sensitive adhesive process film
44=punch
45=transport roller
46=tension roll to the transport roller
47=rolling-up of punched screen

The invention claimed is:

1. An adhesive functional strip for transcutaneous fluorescence measurement of general organ functions or metabolic organ disorders by a sensor, characterised in that the strip consists of a laminate of layers in the following order:
   a backing-less transparent transfer adhesive strip or transparent adhesive tape provided on both sides with a pressure-sensitive adhesive coating provided for direct application to the skin;
   a transparent film;
   at least one light-absorbing pressure-sensitive adhesive layer for absorbing diffused light so that a fluorescence measurement is not disturbed, comprising at least one recess representing an optical window for the sensor to examine the skin; and
   a stabilizing transparent cover stabilizing the entire strip.

2. The adhesive functional strip according to claim 1, characterised in that a circumferential sealing frame comprising four sealing strips is applied on a side of the adhesive functional strip which is remote from the skin, the production of which frame is particularly integrated in the production process of the functional patch, and which thus is an integral component of the functional patch.

3. The adhesive functional strip according to claim 1, characterised in that the transfer adhesive strip or the transparent adhesive tape which is suitable and approved for applications to the skin comprises an adhesive on the basis of either acrylate, silicone or rubber.

4. The adhesive functional strip according to claim 1, characterised in that the at least one light-absorbing pressure-sensitive adhesive layer consists of a soot-pigmented and consequently black adhesive on the basis of acrylate, silicone or rubber.

5. The adhesive functional strip according to claim 1, characterised in that the light-absorbing pressure-sensitive adhesive layer is present in the form of a backing-based adhesive tape provided on both sides with a soot-pigmented and consequently black adhesive on the basis of acrylate, silicone or rubber.

6. The adhesive functional strip according to claim 1, characterised in that the light-absorbing pressure-sensitive adhesive layer(s) contains/contain a recess therethrough to provide a direct light contact both of a sensor head which is equipped with LED light and also of a photodiode with the skin.

7. The adhesive functional strip according to claim 1, characterised in that the double-sided light-absorbing adhesive tape contains a plurality of window-shaped recesses therethrough located next to one another and separated from one another by light-impermeable webs, to provide a direct light contact both of a sensor head equipped with LED light and also of a photodiode with the skin.

8. The adhesive functional strip according to claim 2, characterised in that the sealing strips consist of a foam coated on both sides with an adhesive on the basis of acrylate, silicone or rubber.

9. The adhesive functional strip according to claim 1, characterised in that the strip is reusable several times.

10. The adhesive functional strip according to claim 1, wherein a circumferential sealing frame comprising four sealing strips is applied on a side of the adhesive functional strip which is remote from the skin, wherein the adhesive functional patch is present as one of a separate sealing frame which is to be attached before the application of the sensor, and as a sealing frame which is connected to the sensor and therefore is to be fastened simultaneously with the application of the sensor.

11. The adhesive functional strip according to claim 1, wherein the adhesive functional strip is a disposable product.

* * * * *